(12) United States Patent
Noda et al.

(10) Patent No.: US 10,568,980 B2
(45) Date of Patent: Feb. 25, 2020

(54) NOZZLE-TYPE ELECTRON BEAM IRRADIATION DEVICE, AND ELECTRON BEAM STERILIZATION EQUIPMENT EQUIPPED WITH SAME

(71) Applicant: HITACHI ZOSEN CORPORATION, Osaka (JP)

(72) Inventors: Takeshi Noda, Osaka (JP); Ichiro Sakai, Osaka (JP); Hiroyuki Daiku, Osaka (JP)

(73) Assignee: HITACHI ZOSEN CORPORATION, Osaka (JP)

( * ) Notice: Subject to any disclaimer, the term of this patent is extended or adjusted under 35 U.S.C. 154(b) by 0 days.

(21) Appl. No.: 16/094,312

(22) PCT Filed: Dec. 26, 2016

(86) PCT No.: PCT/JP2016/088683
§ 371 (c)(1),
(2) Date: Oct. 17, 2018

(87) PCT Pub. No.: WO2017/183235
PCT Pub. Date: Oct. 26, 2017

(65) Prior Publication Data
US 2019/0134241 A1 May 9, 2019

(30) Foreign Application Priority Data
Apr. 18, 2016 (JP) .................................. 2016-082553

(51) Int. Cl.
| A61L 2/08 | (2006.01) |
| B65B 55/08 | (2006.01) |
| G21K 5/04 | (2006.01) |
| G21K 5/10 | (2006.01) |
(Continued)

(52) U.S. Cl.
CPC ................. *A61L 2/087* (2013.01); *A61L 2/08* (2013.01); *B65B 55/04* (2013.01); *B65B 55/08* (2013.01);
(Continued)

(58) Field of Classification Search
CPC ...................................................... A61L 2/087
See application file for complete search history.

(56) References Cited

U.S. PATENT DOCUMENTS

| 2,899,556 A | 8/1959 | Schopper et al. |
| 2007/0145304 A1* | 6/2007 | Roche ..................... A61L 2/087 |
| | | 250/493.1 |

(Continued)

FOREIGN PATENT DOCUMENTS

| DE | 1253841 B | 11/1967 |
| JP | 47-041318 B | 10/1972 |
(Continued)

OTHER PUBLICATIONS

International Search Report PCT/JP2016/088683 dated Mar. 28, 2017 with English translation.
(Continued)

*Primary Examiner* — Donald R Spamer
(74) *Attorney, Agent, or Firm* — Pillsbury Winthrop Shaw Pittman, LLP

(57) ABSTRACT

A nozzle-type electron beam irradiation device includes a vacuum chamber, an electron beam generator disposed in the vacuum chamber, and a vacuum nozzle that is connected to the vacuum chamber so as to guide an electron beam from the electron beam generator and emit the electron beam to the outside. The nozzle-type electron beam irradiation device includes a high-vacuum pump capable of sucking gas from the vicinity of the connecting part of the vacuum nozzle in the vacuum chamber.

6 Claims, 12 Drawing Sheets

(51) Int. Cl.
*H01J 37/18* (2006.01)
*H01J 37/16* (2006.01)
*B65B 55/04* (2006.01)
*H01J 33/02* (2006.01)

(52) U.S. Cl.
CPC ............... *G21K 5/04* (2013.01); *G21K 5/10* (2013.01); *H01J 33/02* (2013.01); *H01J 37/165* (2013.01); *H01J 37/18* (2013.01); *H01J 2237/0264* (2013.01); *H01J 2237/1825* (2013.01)

(56) References Cited

U.S. PATENT DOCUMENTS

2007/0228275 A1* 10/2007 Fuse .................. B82Y 10/00
250/310
2011/0012030 A1* 1/2011 Bufano ................ A61L 2/087
250/492.3

FOREIGN PATENT DOCUMENTS

| JP | 2854466 B | 2/1999 |
| JP | 2008-128969 A | 6/2008 |
| JP | 2009-068973 A | 4/2009 |

OTHER PUBLICATIONS

Extended European Search Report dated Oct. 21, 2019 issued in corresponding EP Application No. 16899506.6.

\* cited by examiner

F I G. 6
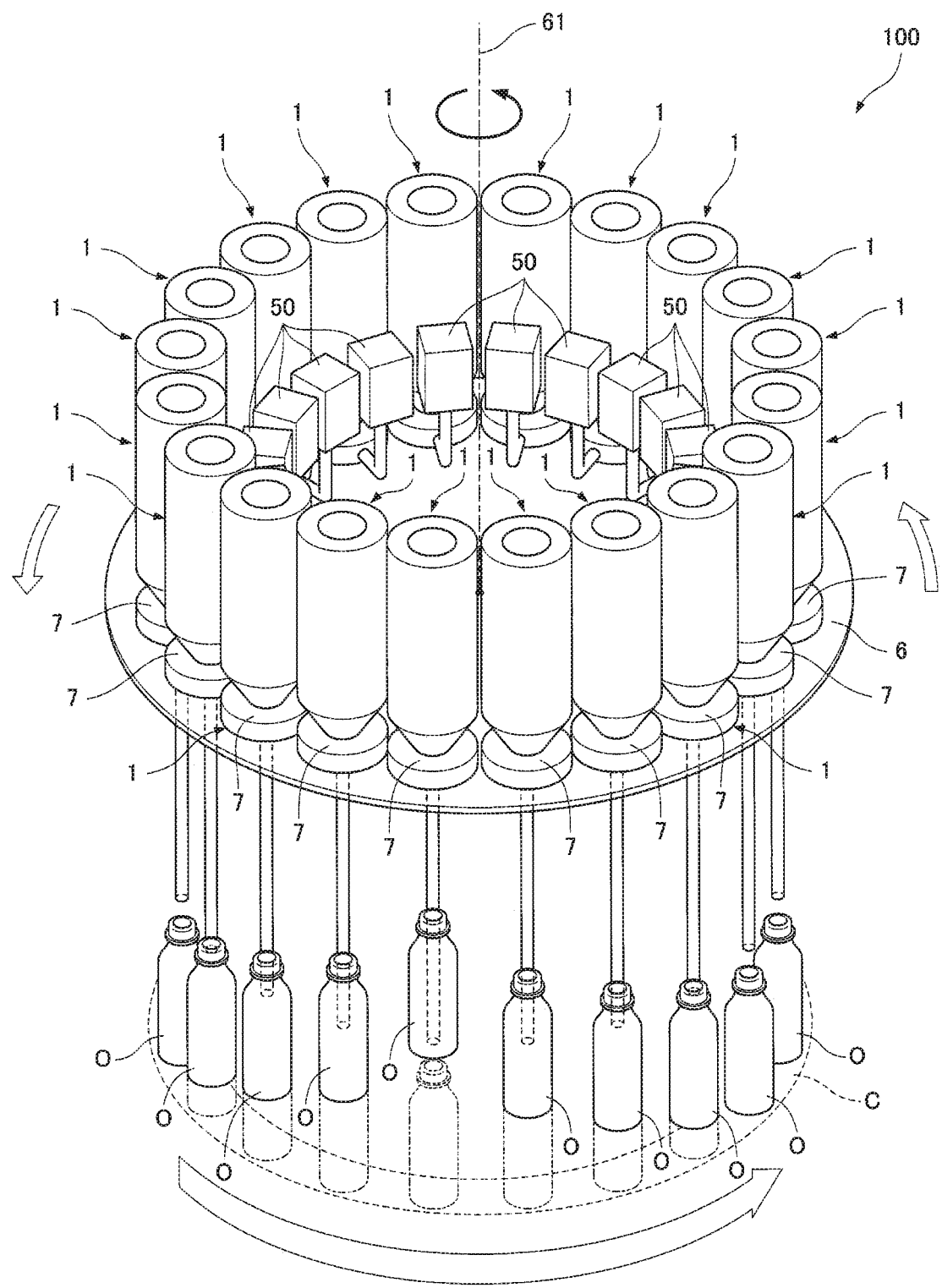

NOZZLE-TYPE ELECTRON BEAM IRRADIATION DEVICE, AND ELECTRON BEAM STERILIZATION EQUIPMENT EQUIPPED WITH SAME

CROSS-REFERENCE TO RELATED APPLICATIONS

This is the U.S. National Stage of PCT/JP2016/088683, filed Dec. 26, 2016, which in turn claims priority to Japanese Patent Application No. 2016-082553, filed Apr. 18, 2016, the contents of each of these applications being incorporated herein by reference in their entireties.

TECHNICAL FIELD

The present invention relates to a nozzle-type electron beam irradiation device and electron beam sterilization equipment equipped with the same.

BACKGROUND ART

A nozzle-type electron beam irradiation device provided in electron beam sterilization equipment emits an electron beam from a vacuum nozzle of the sterilization equipment and thus an electron beam can be emitted to the inner surface of a sterilization object such as a container from the tip of the vacuum nozzle inserted from the mouth of the container. In other words, in such electron beam sterilization equipment, the inner surface of a container is sterilized by direct irradiation with an electron beam from a nozzle-type electron beam irradiation device, thereby suppressing the intensity of the emitted electron beam. Thus, the electron beam sterilization equipment can reduce power consumption and suppress the irradiation of a strong electron beam so as to reduce the deterioration of the container, as compared with equipment for sterilizing the inner surface of a container by irradiation with a strong electron beam from the outside of the container.

In an electron beam irradiation device such as a nozzle-type electron beam irradiation device, the inside of a vacuum chamber needs to be placed in a high-vacuum atmosphere by a high-vacuum pump in order to accelerate an electron beam emitted from the source of the electron beam. In this case, the source of the electron beam also generates gas with heat for generating the electron beam and thus the high-vacuum pump is preferably disposed near the source of the electron beam. According to the related art, a device with a high-vacuum pump (specifically, an ion pump) disposed near the source of an electron beam is proposed (for example, see Patent Literature 1).

CITATION LIST

Patent Literature

Patent Literature 1: Japanese Patent No. 2854466

SUMMARY OF INVENTION

Technical Problem

If the layout of the ion pump described in Patent Literature 1 is applied to a nozzle-type electron beam irradiation device, gas "a" from an electron beam source 3 is immediately discharged by an ion pump 50 as shown in FIG. 13. However, an electron beam E of the nozzle-type electron beam irradiation device is guided through a long vacuum nozzle 4 and tends to travel in various directions due to disturbance such as terrestrial magnetism, so that the electron beam E may hit the inner surface of the vacuum nozzle 4. In this case, gas "b" is generated from the inner surface of the vacuum nozzle 4. Since the ion pump 50 is separated from the vacuum nozzle 4 serving as the source of the gas "b", the degree of vacuum is low near the connecting part of the vacuum nozzle 4 in a vacuum chamber 2. On the other hand, the degree of vacuum is high near the connecting part of the ion pump 50 in the vacuum chamber 2. Thus, in the nozzle-type electron beam irradiation device, the degree of vacuum is unevenly distributed in the vacuum chamber 2, leading to difficulty in proper irradiation of an electron beam.

An object of the present invention is to provide a nozzle-type electron beam irradiation device capable of emitting a proper electron beam by substantially evenly distributing the degree of vacuum in a vacuum chamber, and electron beam sterilization equipment equipped with the irradiation device.

Solution to Problem

In order to solve the problem, a nozzle-type electron beam irradiation device according to a first invention includes a vacuum chamber, an electron beam generator disposed in the vacuum chamber, and a vacuum nozzle that is connected to the vacuum chamber so as to guide an electron beam from the electron beam generator and emit the electron beam to the outside, the nozzle-type electron beam irradiation device further including a high-vacuum pump capable of sucking gas from the vicinity of the connecting part of the vacuum nozzle in the vacuum chamber.

In a nozzle-type electron beam irradiation device according to a second invention, the high-vacuum pump in the nozzle-type electron beam irradiation device according to the first invention is an ion pump, and the ion pump is provided with a magnetic shielding member that prevents a magnetic field from the ion pump from of an electron beam generated from the electron beam generator.

In a nozzle-type electron beam irradiation device according to a third invention, the magnetic shielding member in the nozzle-type electron beam irradiation device according to the second invention is a magnetic shield surrounding the ion pump.

Moreover, in a nozzle-type electron beam irradiation device according to a fourth invention, the magnetic shielding member in the nozzle-type electron beam irradiation device according to the second invention is a retraction pipe that connects the ion pump and the vacuum chamber and places the ion pump at a retraction position.

Electron beam sterilization equipment according to a fifth invention includes:
a turn table having the at least one nozzle-type electron beam irradiation device according to any one of the first to fourth inventions; and a flange that fixes the nozzle-type electron beam irradiation device on the turn table,
the flange connecting the vacuum chamber, the vacuum nozzle, and the high-vacuum pump of the nozzle-type electron beam irradiation device.

In electron beam sterilization equipment according to a sixth invention, the high-vacuum pump in the electron beam sterilization equipment according to the fifth invention faces the center of the turn table.

Electron beam sterilization equipment according to a seventh invention, in the electron beam sterilization equipment according to the fifth invention, is configured such that the at least one nozzle-type electron beam irradiation device disposed on the turn table includes a plurality of nozzle-type electron beam irradiation devices, the high-vacuum pump of the nozzle-type electron beam irradiation device faces the outside of the turn table and is disposed between the adjacent nozzle-type electron beam irradiation devices, and the magnetic shielding member of the nozzle-type electron beam irradiation device prevents a magnetic field from the ion pump of the nozzle-type electron beam irradiation device from affecting an electron beam generated from the electron beam generator of the adjacent nozzle-type electron beam irradiation device.

Advantageous Effects of Invention

According to the nozzle-type electron beam irradiation device, the degree of vacuum is substantially evenly distributed in the vacuum chamber and the vacuum nozzle, thereby emitting a proper electron beam. Moreover, according to the electron beam sterilization equipment equipped with the nozzle-type electron beam irradiation device, the nozzle-type electron beam irradiation device is structurally stabilized so as to reduce an electron beam loss caused by deformation of the device. This allows emission of a proper electron beam.

BRIEF DESCRIPTION OF DRAWINGS

FIG. 6 is a perspective view showing the electron beam sterilization equipment equipped with the nozzle-type electron beam irradiation device.

DESCRIPTION OF EMBODIMENT

A nozzle-type electron beam irradiation device and electron beam sterilization equipment equipped with the same according to an embodiment of the present invention will be described below.

Figure 1:
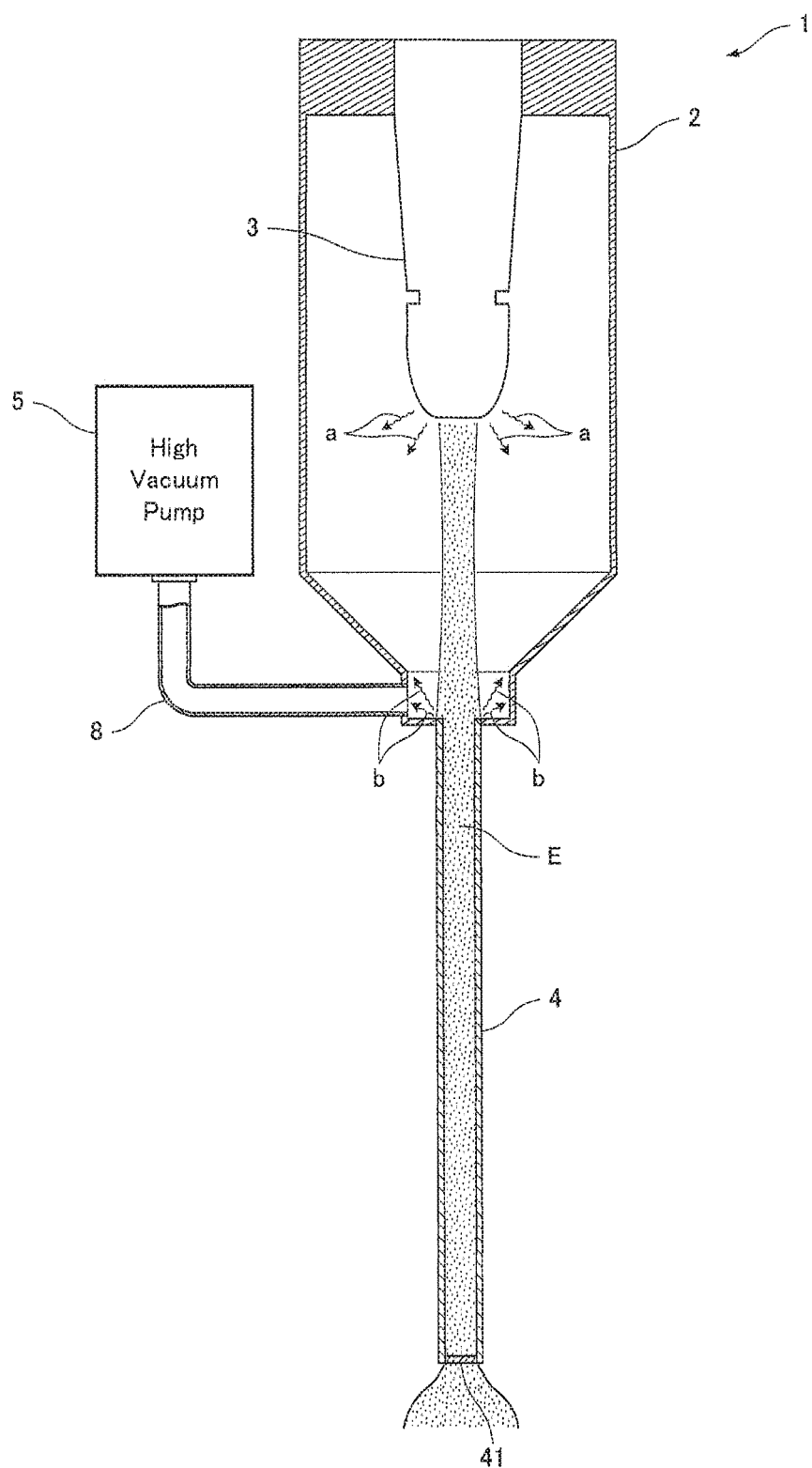
FIG. 1 is a schematic vertical cross-sectional view showing a nozzle-type electron beam irradiation device according to an embodiment of the present invention.

Referring to FIG. 1, the nozzle-type electron beam irradiation device will be first described below.

As shown in FIG. 1, the nozzle-type electron beam irradiation device includes a vacuum chamber 2, an electron beam generator 3 disposed in the vacuum chamber 2, and a vacuum nozzle 4 that is connected to the vacuum chamber 2 so as to guide an electron beam E from the electron beam generator 3 and emit the electron beam E to the outside. The nozzle-type electron beam irradiation device 1 further includes a high-vacuum pump 5 that can suck gas from the vicinity of the connecting part of the vacuum nozzle 4 in the vacuum chamber 2.

The inside of the vacuum chamber 2 is placed in a high-vacuum atmosphere, which is suitable for acceleration of the electron beam E, with the vacuum nozzle 4 by the suction of the high-vacuum pump 5. The electron beam generator 3 is disposed such that the generated electron beam E travels from the proximal end (near the vacuum chamber 2) to the tip (opposite from the vacuum chamber 2) of the vacuum nozzle 4. The vacuum nozzle 4 is configured to emit the guided electron beam E from the tip of the nozzle to the outside and has a transmission window 41, through which the electron beam E can be transmitted, at the tip of the nozzle. The high-vacuum pump 5 is connected to the vacuum chamber 2 and thus properly discharges gas "a" from the electron beam generator 3 disposed in the vacuum chamber 2. Moreover, the high-vacuum pump 5 is connected around the proximal end of the vacuum nozzle 4 and thus properly discharges gas "b" from the vacuum nozzle 4. The high-vacuum pump 5 may be directly connected near the proximal end the vacuum nozzle 4 or connected via a pipe like an L pipe 8 as shown in FIG. 1.

With this configuration, the electron beam E generated by the electron beam generator 3 is accelerated in the vacuum chamber 2 and the vacuum nozzle 4, is guided from the proximal end to the tip of the vacuum nozzle 4, and then is emitted from the tip to the outside. At this point, the gas "a" produced by generating the electron beam E in the electron beam generator 3 and the gas "b" produced by the electron beam E colliding with the inner surface of the vacuum nozzle 4 are properly discharged by the high-vacuum pump 5. The electron beam E hits the inner surface of the vacuum nozzle 4 because the electron beam E is set slightly larger in diameter (e.g., by about 10%) than the vacuum nozzle 4 in order to stabilize the output of the electron beam E from the irradiation window 41, for that the electron beam E is susceptible to disturbance such as terrestrial magnetism.

As described above, the nozzle-type electron beam irradiation device 1 properly discharges the gas "a" and "b" from the electron beam generator 3 and the vacuum nozzle 4 so as to substantially evenly distribute the degree of vacuum in the vacuum chamber 2. This allows emission of the proper electron beam E.

Figure 2:
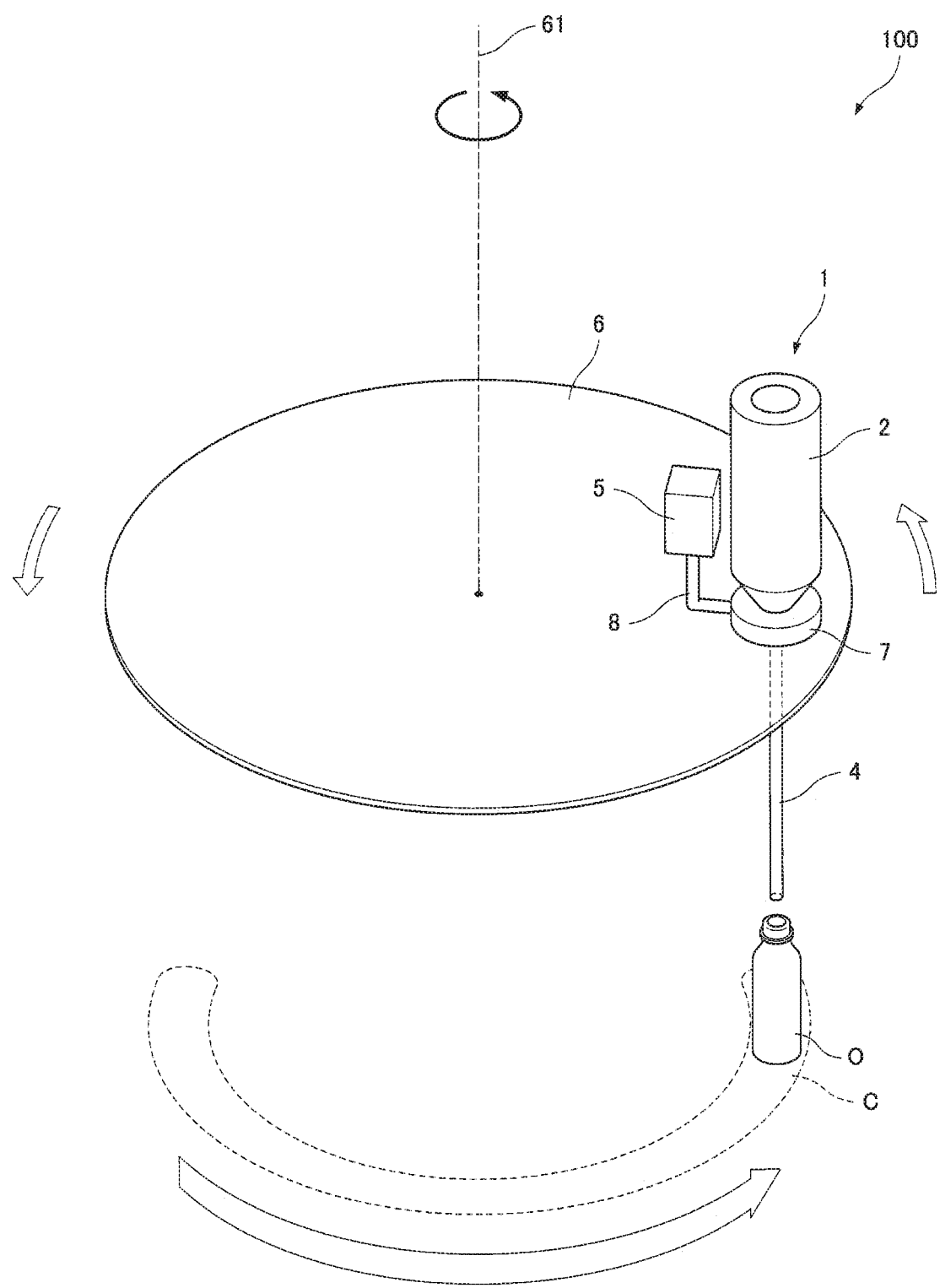
FIG. 2 is a schematic perspective view showing electron beam sterailization equipment equipped with the nozzle-type electron beam irradiation device.

Referring to FIG. 2, the electron beam sterilization equipment equipped with the nozzle-type electron beam irradiation device 1 will be described below.

As shown in FIG. 2, the electron beam sterilization equipment includes a turn table 6 having the nozzle-type electron beam irradiation device 1 on the outer edge of the turn table 6, and a flange 7 that fixes the nozzle-type electron beam irradiation device 1 on the turn table 6. The flange 7 connects the vacuum chamber 2, the vacuum nozzle 4, and the high-vacuum pump 5 of the nozzle-type electron beam irradiation device 1.

The turn table 6 rotates on a center 61 so as to circumferentially move the nozzle-type electron beam irradiation device 1 disposed on the outer edge of the turn table 6. With this configuration, the nozzle-type electron beam irradiation device 1 can sterilize a sterilization object O (e.g., a container or a preform) by irradiation with the electron beam E while tracking the sterilization object O conveyed on a circular passage C. Additionally, the turn table 6 allows the nozzle-type electron beam irradiation device 1 in a static state (not conveyed) to sequentially sterilize the multiple sterilization objects O disposed on the circular passage C by irradiation with the electron beam E. Thus, the electron beam sterilization equipment 100 equipped with the nozzle-type electron beam irradiation device 1 disposed on the outer edge of the turn table 6 is suitable for sequentially sterilizing the sterilization objects O.

With this configuration, the nozzle-type electron beam irradiation device 1 provided in the electron beam sterilization equipment 100 receives a centrifugal force by the rotation of the turn table 6. However, the flange 7 fixed on the turn table 6 connects the vacuum chamber 2, the vacuum nozzle 4, and the high-vacuum pump 5, thereby structurally stabilizing the nozzle-type electron beam irradiation device 1.

As described above, according to the electron beam sterilization equipment 100, the nozzle-type electron beam irradiation device 1 is structurally stabilized so as to reduce a loss of the electron beam E, the loss being caused by deformation of the device. This allows emission of the proper electron beam E.

Example

The nozzle-type electron beam irradiation device 1 and the electron beam sterilization equipment 100 equipped with the same will be described below according to a specific example of the embodiment.

Figure 3:
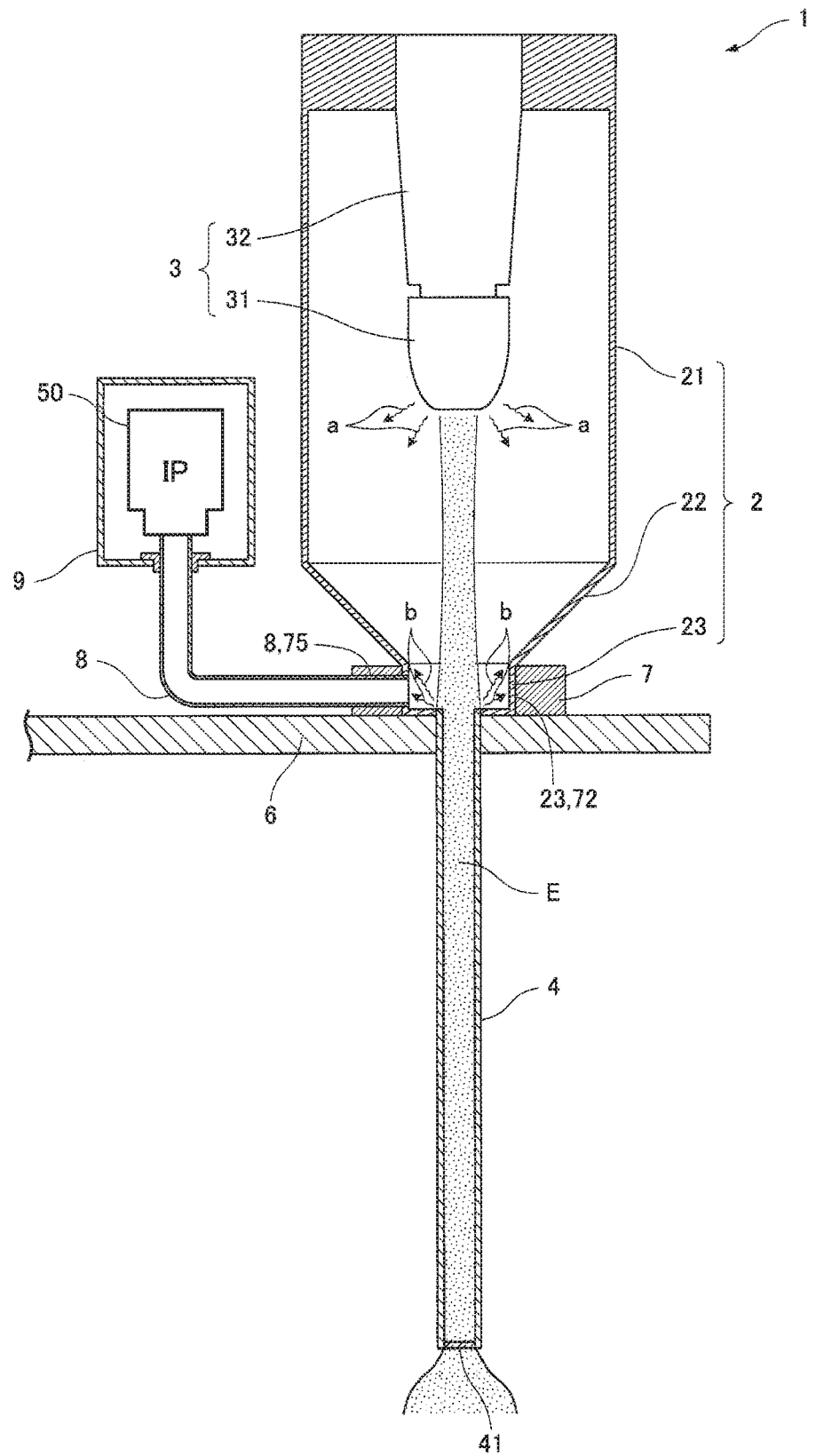
FIG. 3 is a vertical cross-sectional view showing the nozzle-type electron beam irradiation device according to an example of the present invention.

Referring to FIG. 3, the nozzle-type electron beam irradiation device 1 will be first described below.

As shown in FIG. 3, the nozzle-type electron beam irradiation device 1 includes the vacuum chamber 2, the electron beam generator 3 disposed in the vacuum chamber 2, and the vacuum nozzle 4 that is connected to the vacuum chamber 2 so as to guide the electron beam E from the electron beam generator 3 and emit the electron beam E to the outside. The nozzle-type electron beam irradiation device 1 further includes an ion pump 50 (an example of the high-vacuum pump 5) that can suck gas from the vicinity of the connecting part of the vacuum nozzle 4 in the vacuum chamber 2.

The vacuum chamber 2 has a cylindrical part 21 shaped like a large cylinder, a diameter-reducing part 22 that continues from the cylindrical part 21 and tapers in the traveling direction of the electron beam E, and a connecting part 23 shaped like a small cylinder continues from the diameter reducing part 22.

The electron beam generator 3 includes an electron gun that generates the electron beam E from an electron source (e.g., a filament or a cathode, not shown) by power supply, and a holding part 32 that holds the electron gun 31 and is attached to the cylindrical part 21 of the vacuum chamber 2. The electron beam generator 3 further includes a power supply unit (not shown) for supplying power to the electron gun 31 (for example, the power supply unit is disposed outside the vacuum chamber 2).

The vacuum nozzle 4 has the proximal end connected to the connecting part 23 of the vacuum chamber 2 and the tip, from which the electron beam E emitted to the outside, on the opposite side from the proximal end. Moreover, the vacuum nozzle 4 has the transmission window 41, through which the electron beam E can be transmitted, at the tip of the nozzle.

The ion pump 50 includes the L pipe 8 connecting to the connecting part 23 of the vacuum chamber 2 and a magnetic shield 9 (an example of a magnetic shielding member) that prevents a magnetic field from the ion pump 50 from affecting the electron beam E.

In the present embodiment, the flange 7 described as a component of the electron beam sterilization equipment 100 may be a component of the nozzle-type electron beam irradiation device 1. In this example, the flange 7 will be described as a component of the nozzle-type electron beam irradiation device 1. The flange 7 is a disk fixed on a mount such as the turn table 6 with a fixture (e.g., a bolt and a nut, not shown). The disk constituting the flange 7 has a through hole 72 penetrating both surfaces of the disk and a lateral hole 75 communicating from the through hole 72 to the side of the disk. The connecting part 23 of the vacuum chamber 2 is fit into the through hole 72, whereas one end of the L pipe 8 near the vacuum chamber 2 (specifically, near the connecting part 23) is fit into the lateral hole 75.

Figure 4:
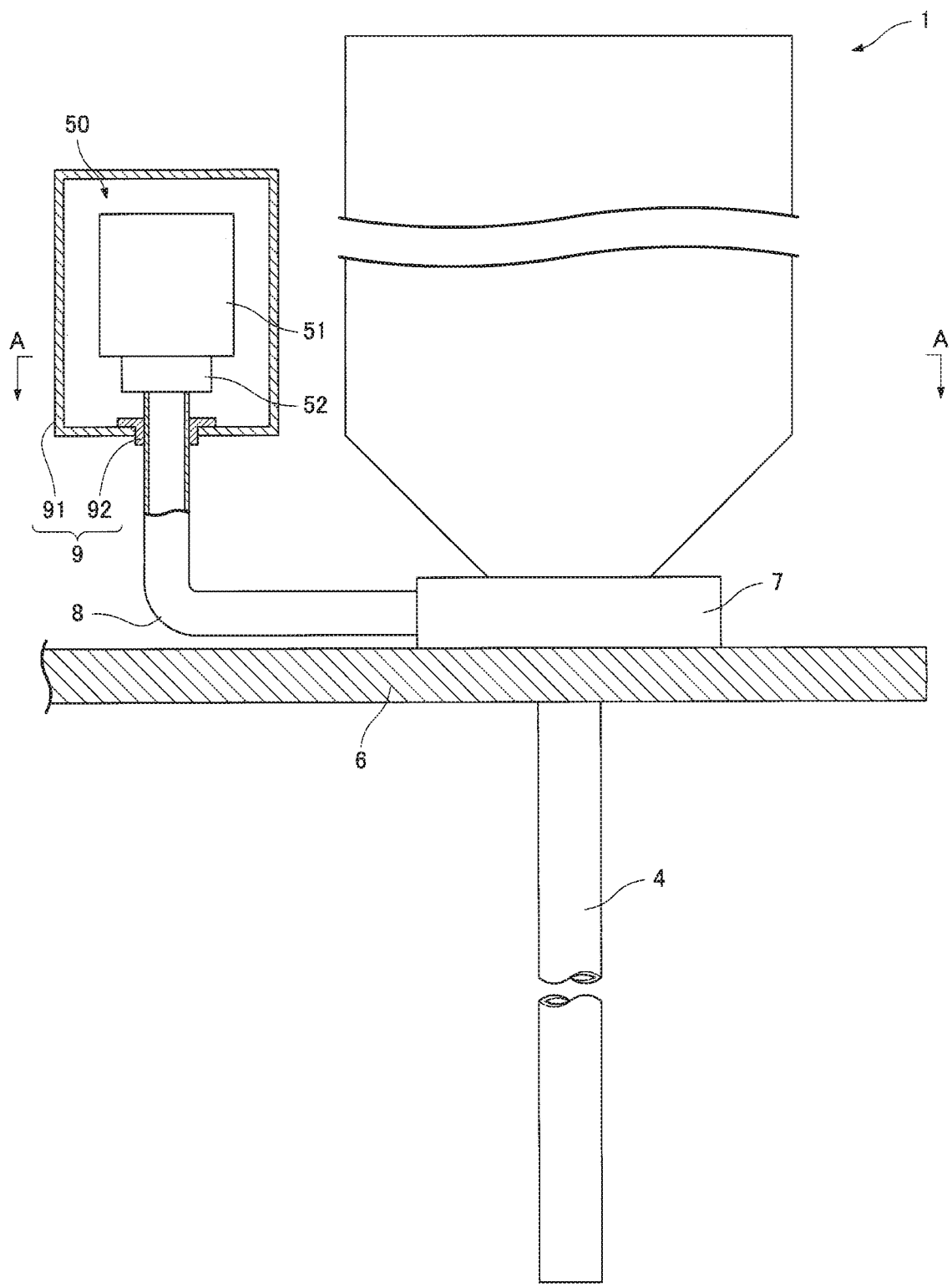
FIG. 4 is a partially-cut vertical cross-sectional view of an enlarged part around an ion pump of the nozzle-type electron beam irradiation device.
Figure 5:
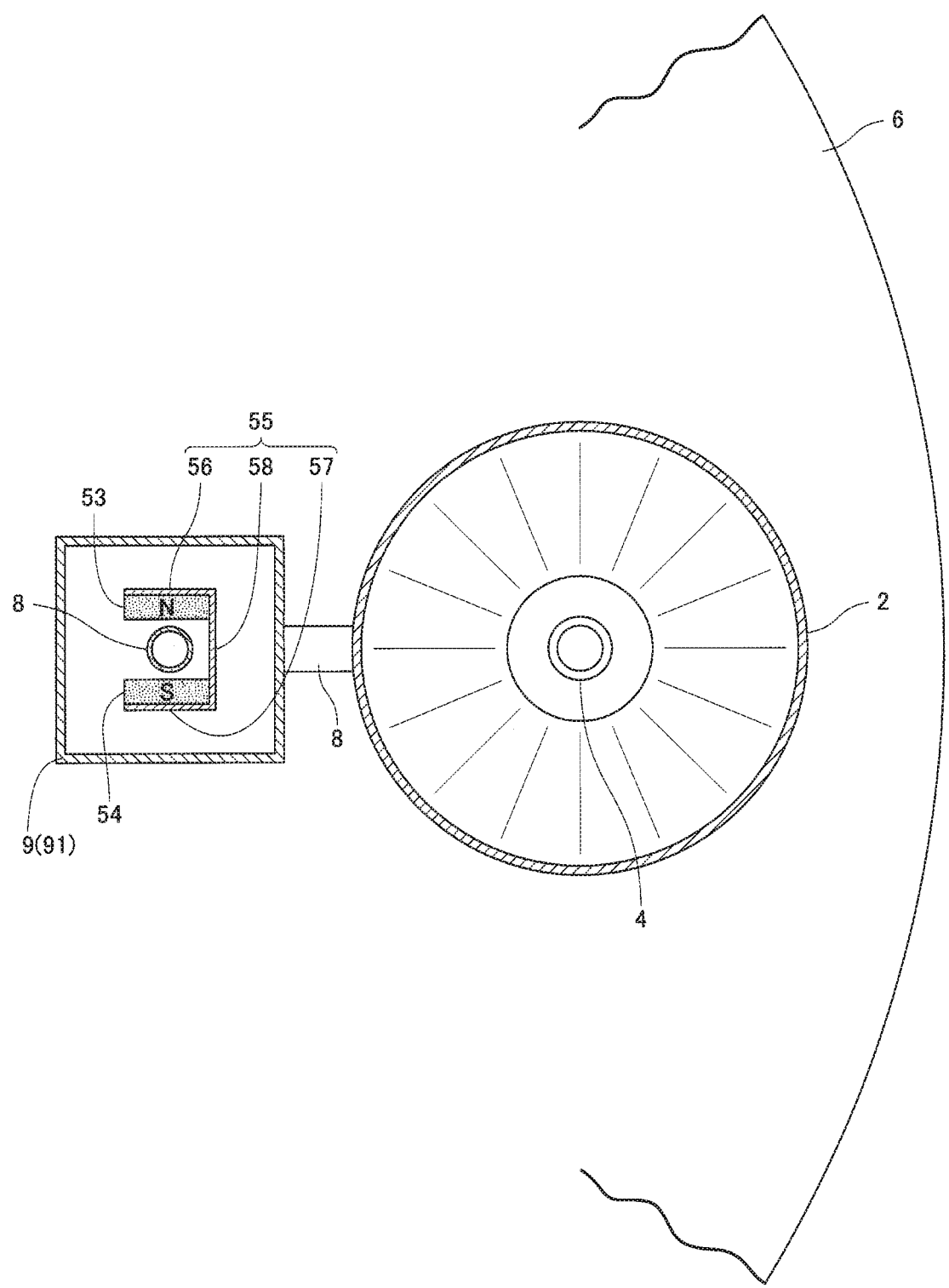
FIG. 5 is a cross-sectional view taken along line A-A of FIG. 4.

Referring to FIGS. 4 and 5, the configurations of the ion pump 50 and the magnetic shield 9 will be specifically described below.

As shown in FIG. 4, the ion pump 50 includes a pump body 51 and a magnet assembly 52 disposed near the L pipe 8. The magnet assembly 52 includes, as shown in FIG. 5, a first magnet 53 and a second magnet 54 (permanent magnets) facing each other. The first magnet 53 has the north pole directed to the south pole of the second magnet 54. The second magnet 54 has the south pole directed to the north pole of the first magnet 53. Furthermore, the magnet assembly 52 includes a yoke 55 for increasing the efficiency of the permanent magnets 53 and 54. The yoke 55 includes a first part 56 that holds the first magnet 53, a second part 57 that holds the second magnet 54, and an intermediate part 58 connecting the first part 56 and the second part 57. The intermediate part 58 of the yoke 55 faces closer one of the vacuum chamber 2 and the vacuum nozzle 4, thereby suppressing the arrival of a line of magnetic force at the electron beam E from the permanent magnets 53 and 54. The placement of the yoke 55 keeps the magnet assembly 52 from considerably affecting the electron beam E (proved also in an experiment by the inventors) even if the ion pump 50 is disposed near the vacuum chamber 2.

The magnetic shield 9 includes, as shown in FIG. 4, a shield body 91 surrounding the ion pump 50 and a tight shield 92 that prevents a line of magnetic force from leaking between the shield body 91 and the L pipe 8.

With this configuration, as shown in FIG. 3, the electron beam E generated by the electron beam generator 3 is accelerated in the vacuum chamber 2 and the vacuum nozzle is guided from the proximal end to the tip of the vacuum nozzle 4, and then is emitted to the outside from the transmission window 41 at the tip of the vacuum nozzle 4. At this point, the gas "a" and the gas "b" are properly discharged by the ion pump 50. The gas "a" is produced by generating the electron beam E in the electron beam generator 3 and the gas "b" is produced by the electron beam E colliding with the inner surface of the vacuum nozzle 4. A magnetic field is generated from the ion pump 50 by the magnet assembly 52. The magnetic shield 9 surrounding the ion pump 50 prevents the magnetic field from affecting the electron beam E from the electron beam generator 3.

As described above, the nozzle-type electron beam irradiation device 1 properly discharges the gas "a" and "b"

from the electron beam generator 3 and the vacuum nozzle 4 so as to substantially evenly distribute the degree of vacuum in the vacuum chamber 2. This allows emission of the proper electron beam E.

Moreover, the nozzle-type electron beam irradiation device 1 is structurally stabilized by the flange 7 so as to reduce a loss of the electron beam E, the loss being caused by deformation of the device. This allows emission of the proper electron beam E.

Furthermore, the magnetic shield 9 surrounding the ion pump 50 prevents a magnetic field from the ion pump 50 from affecting the electron beam from the electron beam generator 3. This allows emission of the proper electron beam E.

Figure 7:
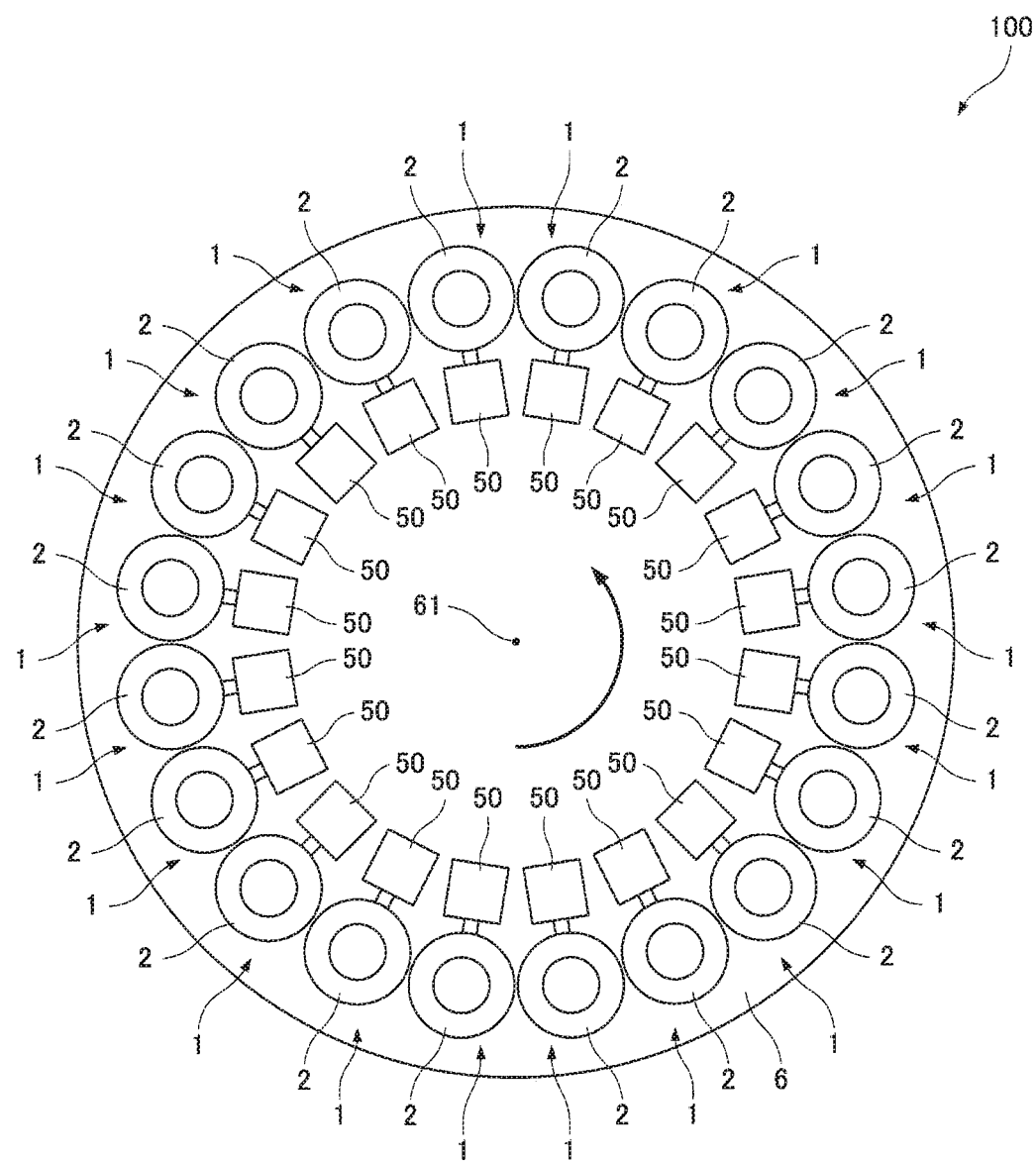
FIG. 7 is a plan view showing the electron beam sterilization equipment.

Referring to FIGS. 6 and 7, the electron beam sterilization equipment 100 equipped with the nozzle-type electron beam irradiation device 1 will be described below.

As shown in FIG. 6, the electron beam sterilization equipment 100 includes the turn table 6 having the nozzle-type electron beam irradiation devices 1 disposed at equal intervals on the outer edge of the turn table 6. The turn table 6 rotates on the center 61 so as to circumferentially move the multiple nozzle-type electron beam irradiation devices 1 disposed on the outer edge of the turn table 6.

The electron beam sterilization equipment 100 includes a conveyor that conveys the sterilization object O on the circular passage C and elevating devices that raise and lower the sterilization objects O conveyed on the circular passage C. The conveyor and the elevating devices are not shown. The conveyor conveys the multiple sterilization objects O, which are disposed below the electron beam irradiation devices 1, on the circular passage C in synchronization with the circular motion of the nozzle-type electron beam irradiation device 1. The elevating device raises and lowers the sterilization object O such that the sterilization object O is brought close to or separated from the nozzle-type electron beam irradiation device 1.

As shown in FIGS. 6 and 7, the electron beam sterilization equipment 100 has the ion pumps 50 facing the center 61 of the turn table 6. Specifically, the ion pump 50 is disposed between the vacuum chamber 2 and the center 61 of the turn table 6 in each of the nozzle-type electron beam irradiation devices 1.

With this configuration, the nozzle-type electron beam irradiation device 1 provided in the electron beam sterilization equipment 100 receives a centrifugal force by the rotation of the turn table 6. However, the flange 7 fixed on the turn table 6 connects the vacuum chamber 2, the vacuum nozzle 4, and the high-vacuum pump 5, thereby structurally stabilizing the nozzle-type electron beam irradiation device 1. Moreover, the ion pump 50 is disposed between the vacuum chamber 2 and the center 61 of the turn table 6, the center of gravity of the nozzle-type electron beam irradiation device 1 is located close to the center 61 of the turn table 6.

As described above, according to the electron beam sterilization equipment 100, the nozzle-type electron beam irradiation device 1 is structurally stabilized so as to reduce a loss of the electron beam E, the loss being caused by deformation of the device. This allows emission of the proper electron beam E.

Moreover, the ion pump 50 is disposed between the vacuum chamber 2 and the center 61 of the turn table 6, thereby reducing the size of the equipment.

Furthermore, the center of gravity of the nozzle-type electron beam irradiation device 1 is located close to the center 61 of the turn table 6, thereby reducing a centrifugal force applied to the nozzle-type electron beam irradiation device 1. This reduces a loss of the electron beam E, the loss being caused by deformation of the device, and thus allows emission of the proper electron beam E.

Figure 8:
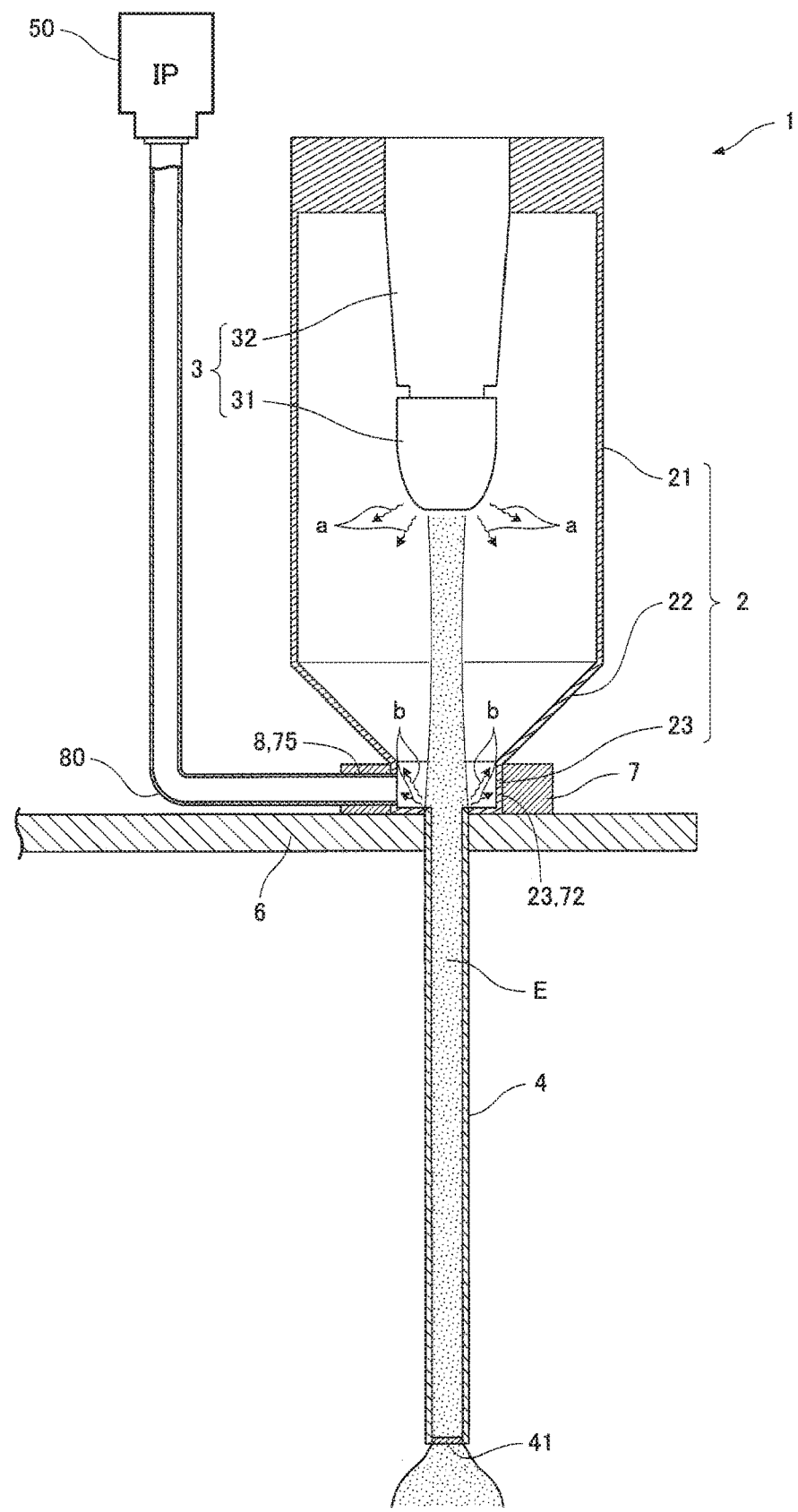
FIG. 8 is a vertical cross-sectional view showing another example of the nozzle-type electron beam irradiation device.

In this example, the magnetic shield 9 was described as an example of a magnetic shielding member. As shown in FIG. 8, the ion pump 50 may be disposed at a retraction position in the absence of the magnetic shield 9. The retraction position is a position where a magnetic field from the ion pump 50 does not affect the electron beam E from the electron beam generator 3. For example, as shown in FIG. 8, the ion pump 50 is removed on the opposite side from the vacuum nozzle 4 of the vacuum chamber 2. In order to dispose the ion pump 50 at the retraction position, the L pipe 8 may be replaced with an elongated longitudinal pipe 80 shown in FIG. 8 or an elongated lateral directed pipe (not shown). The ion pump 50 at the retraction position and the vacuum chamber 2 are connected to each other via the retraction pipe 80. The retraction pipe 80 may have any shaped other than an L-shape as long as the ion pump 50 is disposed at the retraction position.

Figure 9:
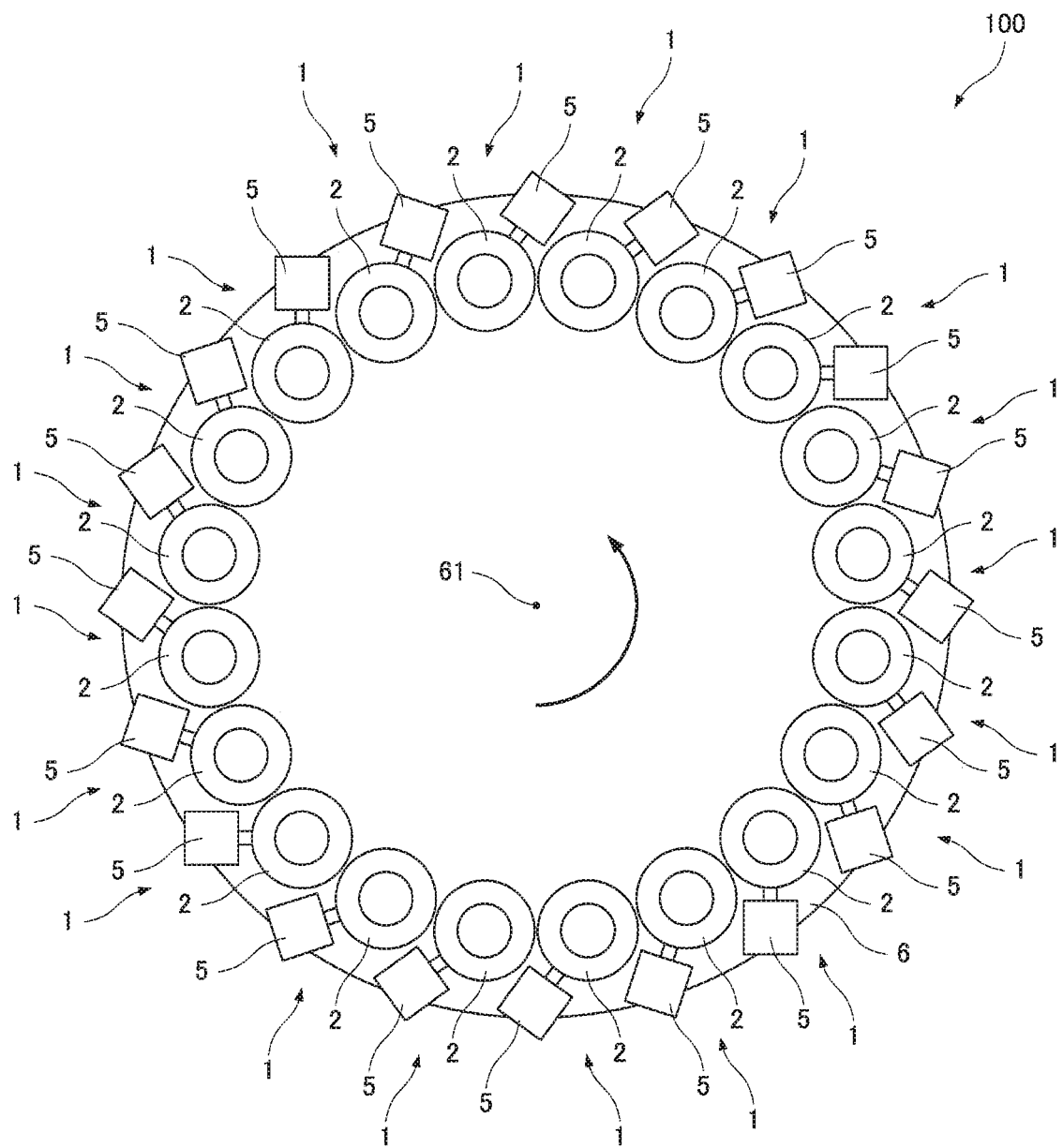
FIG. 9 is a plan view showing another example of the electron beam sterilization equipment.

In this example, the ion pumps 50 of the electron beam irradiation device 1 face the center 61 of the turn table 6. The ion pump 50 may be disposed between the adjacent nozzle-type electron beam irradiation devices 1 as shown in FIG. 9. This can reduce the size of the equipment while keeping the ease of maintenance of the ion pump 50.

The ion pump 50 in this example may be replaced with another high-vacuum pump 5. If the high-vacuum pump 5 does not generate a magnetic field, the nozzle-type electron beam irradiation device 1 does not need the magnetic shield 9 and the retraction pipe 80.

Furthermore, the configurations of the example are optional except for the configurations of the present embodiment and can be deleted and changed as necessary.

Figure 10:
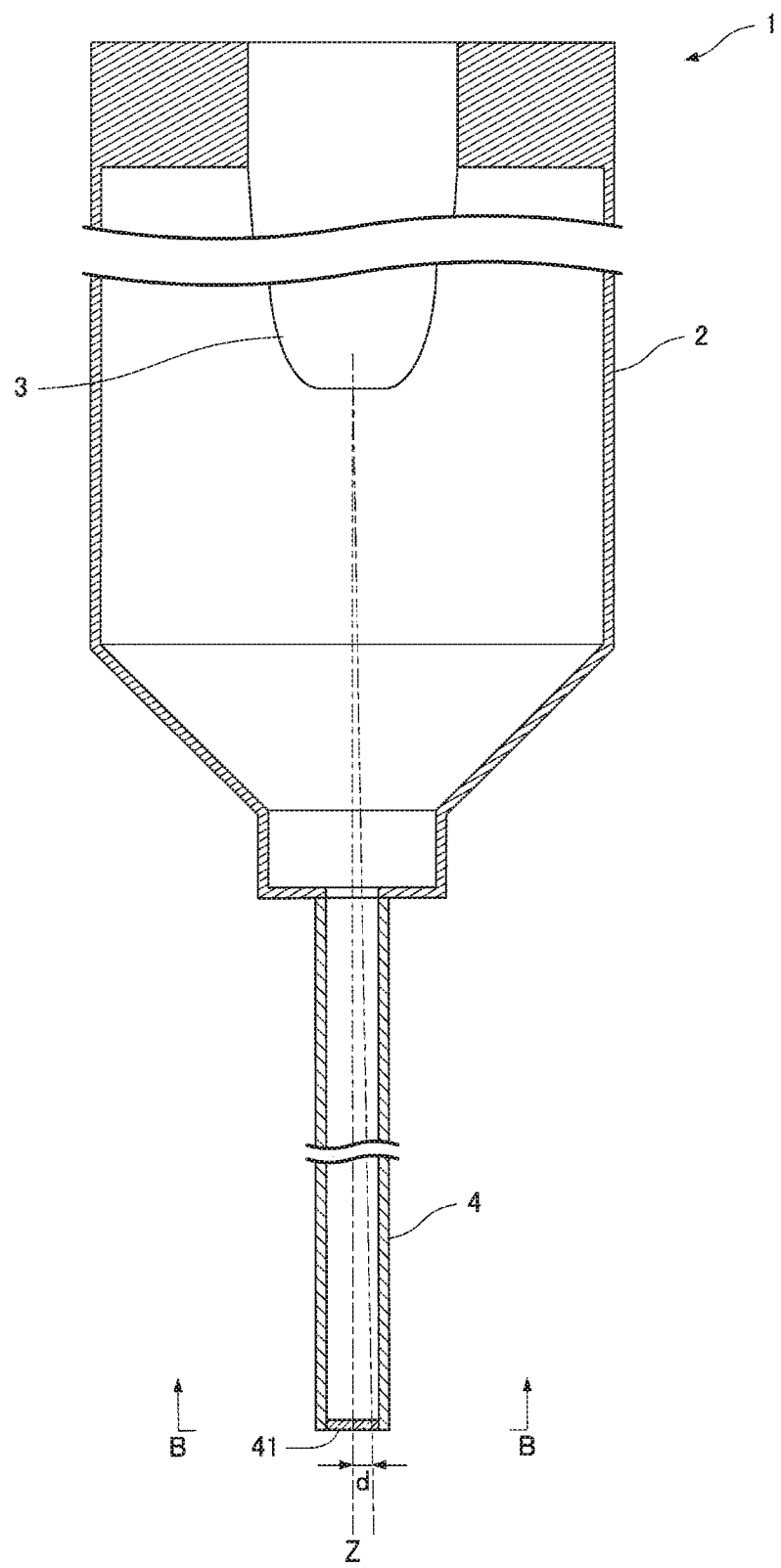
FIG. 10 is a schematic vertical cross-sectional view showing a nozzle-type electron beam irradiation device having a different configuration.

In the present embodiment and the example, the electron beam E is slightly larger (e.g., about 10%) in diameter than the vacuum nozzle 4. This configuration can solve the problem of the related art, that is, unstable output of electron beam emission from a vacuum nozzle to the outside. As shown in FIG. 10, the nozzle-type electron beam irradiation device configured thus is nozzle-type electron beam irradiation device 1 including:

the vacuum chamber 2, the electron beam generator 3 disposed in the vacuum chamber 2, and the vacuum nozzle 4 that is connected to the vacuum chamber 2 so as to guide the electron beam E from the electron beam generator 3 and emit the electron beam E to the outside, wherein the electron beam generator 3 extends along an axis Z of the vacuum nozzle 4 and generates the electron beam E having a larger diameter than the inside diameter of the vacuum nozzle 4.

According to this feature, even if the electron beam E is affected by disturbance, the transverse cross-sectional area of the electron beam E outputted from the vacuum nozzle 4 hardly changes, thereby stabilizing the output of the electron beam E from the vacuum nozzle 4.

In this case, it is preferable that a part 41 (e.g., the irradiation window 41) for outputting the electron beam E from the vacuum nozzle 4 has a virtual diameter that is larger than the inside diameter of the vacuum nozzle 4 in the part 41 by at least twice d that denotes a deviation of the electron beam E in the event of disturbance.

Figure 11:
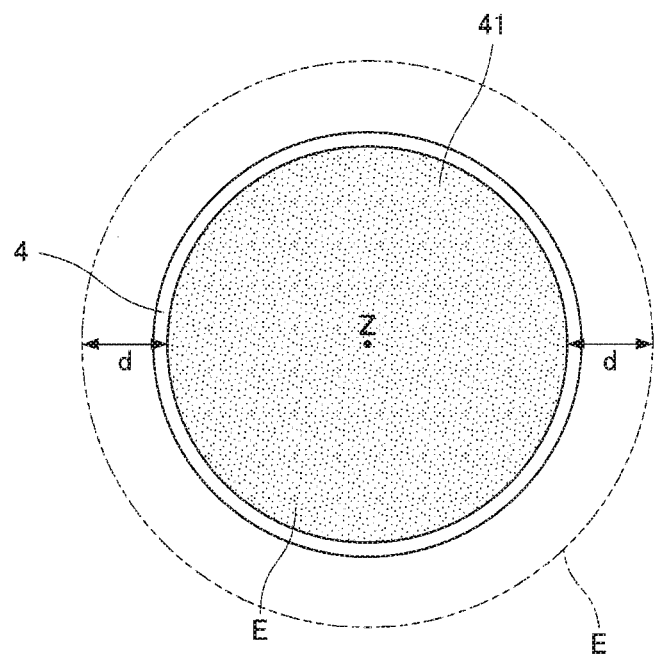
FIG. 11 is a cross-sectional view taken along line B-B of FIG. 10 illustrating an undeviated electron beam.
Figure 12:
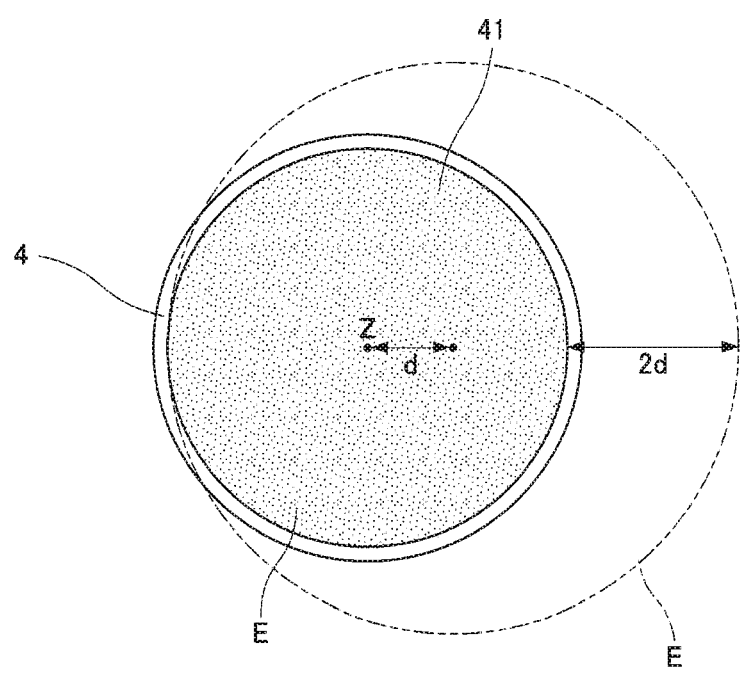
FIG. 12 is a cross-sectional view taken along line B-B of FIG. 10 illustrating a deviated electron beam.
Figure 13:
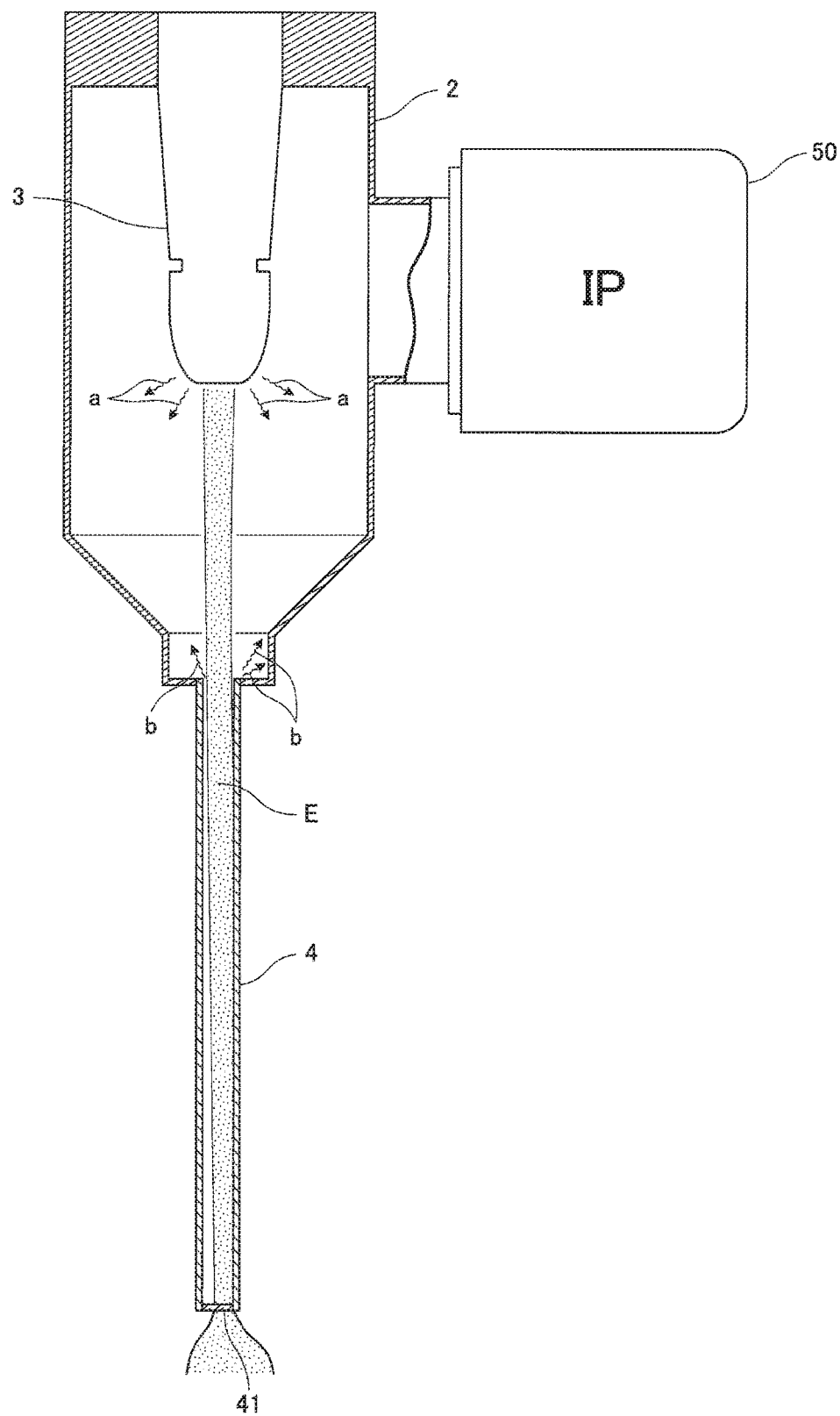
FIG. 13 is a schematic vertical cross-sectional view showing a nozzle-type electron beam irradiation device having an ion pump disposed according to the related art.

FIG. 11 shows that the electron beam E is not deviated by disturbance in the part 41 for outputting the electron beam E from the vacuum nozzle 4. FIG. 12 shows the electron beam E deviated by disturbance. The deviation d of the electron beam E in the event of disturbance is, for example, 5% (doubled to 10%), which is determined in advance by an experiment. As is evident from a comparison between FIG. 11 and FIG. 12, even if the electron beam E is affected by disturbance, the transverse cross-sectional area of the electron beam E outputted from the vacuum nozzle 4 remains constant according to the feature, thereby further stabilizing the output of the electron beam E from the vacuum nozzle 4.

As a matter of course, the configuration in FIGS. 10 to 12 may include at least a part of the configurations of the embodiment and the example.

The invention claimed is:

1. A nozzle-type electron beam irradiation device comprising:
   a vacuum chamber,
   an electron beam generator disposed in the vacuum chamber,
   a vacuum nozzle that is connected to the vacuum chamber via a flange so as to guide an electron beam from the electron beam generator and emit the electron beam to outside of the vacuum nozzle, and
   a high-vacuum pump capable of sucking gas from the vacuum chamber through the flange,
   wherein the vacuum chamber, the vacuum nozzle, and the high-vacuum pump are connected together by the flange.

2. The nozzle-type electron beam irradiation device according to claim 1, wherein the high-vacuum pump is an ion pump, and
   the ion pump is provided with a magnetic shield surrounding the ion pump, the magnetic shield preventing a magnetic field from the ion pump from affecting an electron beam generated from the electron beam generator.

3. The nozzle-type electron beam irradiation device according to claim 1, wherein the high-vacuum pump is an ion pump, and
   the ion pump is provided with a retraction pipe that connects the ion pump and the vacuum chamber and places the ion pump at a retraction position, the retraction pipe preventing a magnetic field from the ion pump from affecting an electron beam generated from the electron beam generator.

4. An electron beam sterilization equipment comprising a turn table having at least one nozzle-type electron beam irradiation device according to claim 1, on an outer edge of the turn table,
   wherein the flange is fixed on the turn table.

5. The electron beam sterilization equipment according to claim 4, wherein the high-vacuum pump faces the center of the turn table.

6. The electron beam sterilization equipment according to claim 4, wherein the at least one nozzle-type electron beam irradiation device disposed on the turn table comprises a plurality of nozzle-type electron beam irradiation devices,
   the high-vacuum pump of each of the plurality of the nozzle-type electron beam irradiation devices faces the outside of the turn table and is disposed between adjacent nozzle-type electron beam irradiation devices.

* * * * *